United States Patent [19]

Caulfield

[11] Patent Number: 4,761,370

[45] Date of Patent: Aug. 2, 1988

[54] METHOD FOR DETERMINING THE PRESENCE OF BACTERIA IN BODY FLUID SPECIMENS CONTAINING BACTERIAL INHIBITORS

[75] Inventor: Michael J. Caulfield, Shaker Hts., Ohio

[73] Assignee: Cleveland Clinic Foundation, Cleveland, Ohio

[21] Appl. No.: 874,638

[22] Filed: Jun. 16, 1986

[51] Int. Cl.$^4$ .................. C12Q 1/14; C12Q 1/02; C12Q 1/06

[52] U.S. Cl. ...................... 435/36; 435/29; 435/39

[58] Field of Search .................. 435/29, 39, 36

[56] References Cited

U.S. PATENT DOCUMENTS 4,145,304  3/1979  Melnick et al.
4,632,902  12/1986  Waters et al. .................. 435/29

*Primary Examiner*—Sam Rosen
*Attorney, Agent, or Firm*—Fay, Sharpe, Beall, Fagan, Minnich & McKee

[57] ABSTRACT

A method for determining the presence of bacteria in a body fluid specimen containing bacterial inhibitors is provided wherein a body fluid specimen containing bacterial inhibitors is procured, and growth media for the bacteria and antibodies specific to the bacterial inhibitors are added to neutralize the effectiveness of the bacterial inhibitors, and after incubation of the reactive mixture the presence of bacteria in the body fluid specimen is determined. An apparatus for accomplishing the foregoing is also provided.

14 Claims, No Drawings

METHOD FOR DETERMINING THE PRESENCE OF BACTERIA IN BODY FLUID SPECIMENS CONTAINING BACTERIAL INHIBITORS

BACKGROUND OF THE INVENTION

A patient suspected of having a bacterial infection is often treated with antibiotics before the bacteria has been isolated and identified. However, this practice can complicate the diagnosis and treatment of the infection since antibiotics prevent the growth of bacteria in ordinary culture media used for the isolation of bacteria. Nevertheless, antibiotics must be given prior to isolation of the bacteria in life threatening situations when the presence of bacteria in the blood (bacteremia) is suspected. In addition, there are certain medical conditions in which it is necessary to know whether a bacterial infection persists even though the bacteria is known to be sensitive to the antibiotic. This can occur, for example, when there is a chronic source of infection such as an abscess or an infection of a heart valve (bacterial endocarditis). Therefore, a method for isolating bacteria from the blood and other body fluids containing antibiotics is desirable.

Conventional methods of identifing the presence of bacteria in the blood and other body fluids containing bacterial inhibitors have proven to be ineffective. Prior methods of inoculating culture media with specimens containing bacterial inhibitors and then determining the presence of turbidity, which indicated bacteria growth, take as long as 14 days because the presence of the bacterial inhibitors hindered the growth of the bacteria, delaying isolation and identification of the bacteria.

A method presently utilized by researchers and physicians to identify and isolate bacteria in body fluid specimens containing bacterial inhibitors involves the use of a detergent-treated resin which selectively removes antibiotics from bacterially infected body fluid specimens without removing the bacteria, see for example U.S. Pat. No. 4,145,304. By removing the bacterial inhibitors while sparing the bacteria, the system disclosed in U.S. Pat. No. 4,145,304, allows the bacteria to be cultured and identified.

Devices or systems which utilizes the resin and method disclosed in U.S. Pat. No. 4,145,304 to remove antimicrobials from body fluids are available commercially. However, utilization of such a device or system involves several steps which limit its practical usage. Generally, the body fluid specimen must be aseptically added to the device or system and then rotated continuously for 15 minutes in order for the resin to absorb the antibiotic. Then, the supernatant mixture must be aseptically removed from the device or system and added to standard culture broth in order to promote growth of the bacteria. The resin, with its absorbed antibiotic, is then discarded. Thus, the use of such a device requires several process steps, including two aseptic transfers, which makes its usage less practical.

An additional disadvantage of the before discussed device is that the resin utilized therein reduces the yield of certain bacteria. Research has indicated that the resin has a direct effect on the growth of Streptococcus (Group A) bacteria and *Escherichia coli*, two organisms readily sought to be isolated and identified by practioneers. Hence, the resin has a number of practical limitations.

A modification of the device and system disclosed in the U.S. Pat. No. 4,145,304 patent process has been developed by Johnston Laboratories, Towson MD. This modification concerns the addition of the resin directly into the culture medium used for the isolation of bacteria. While this modification eliminates the several step limitation of the concerned system, it does not eliminate the effect of the resin on the growth of some bacteria whose identification and isolation is quite crucial to the control and treatment of certain diseases.

In an attempt to overcome the foregoing difficulties, applicant has discovered that supplementing the bacterial growth medium inoculated with a body fluid specimen suspected of containing bacteria with antibodies specific against various bacterial inhibitors, has many advantages over conventionally known methods of isolating and identifying bacteria in body fluid specimens. Applicant's apparatus and method utilizes specific antibodies to neutralize various bacterial inhibitors present in a body fluid specimen, thereby allowing for the growth of otherwise sensitive bacteria. The antibodies react specifically with the bacterial inhibitors and, unlike the resin present in U.S. Pat. No. 4,145,304, do not inhibit growth of any bacteria. In addition, the antibodies utilized within applicant's invention can be kept in solution and, therefore, can easily be added to a wide variety of culture media, allowing for greater versatility than the resin utilized in the herein before discussed prior art process, which cannot readily be transferred aseptically. Accordingly, it is the primary object of the present invention to provide an improved means of rapidly determining the presence of bacteria in body fluid specimens containing bacteria inhibitors without reducing the bacteria count of the specimen.

SUMMARY OF THE INVENTION

In one aspect, the present invention relates to a method for determining the presence of bacteria in a body fluid specimen containing bacterial inhibitors, which method comprises providing a body fluid specimen containing bacterial inhibitors, adding growth media for said bacteria to the body specimen, adding antibodies specific to the bacterial inhibitors to the body fluid specimen to neutralize the effectiveness of the bacterial inhibitors, incubating said reaction mixture and thereafter determining the presence of bacteria in the body fluid specimen.

In another aspect, the present invention concerns an apparatus for determining the presence of bacteria in a body fluid specimen containing bacterial inhibitors, which comprises a vessel containing growth media for said bacteria and antibodies specific to said bacterial inhibitors which neutralize the effectiveness of said bacterial inhibitors, a means of aseptically receiving said body fluid specimen and a means of visually determining the turbidity of the mixture contained therein.

DETAILED DESCRIPTION OF THE INVENTION

The present invention is effective for determining the presence of bacteria in body fluid specimens containing bacterial inhibitors. These specimens, including specimens of blood, urine, spinal fluid, and other body fluids, are obtained by conventionally known methods.

For example, when using the invention with blood specimens, the specimen may be obtained by veinous puncture of a living organism. The specimen is then transferred aseptically to a series of test tubes or culture bottles containing culture medium and various dilutions of antibodies specific to the antibiotic or other bacterial inhibitor present in the specimen. Again, employing conventional methods, the test tubes are incubated, generally at about 37° C., until turbidity is indicated in the culture media manifesting the presence of bacteria. Other methods of determining the presence of bacteria in culture media, such as plating samples of the reaction mixture on various types of selecting growth media, and the determination of the radioactive carbon dioxide utilization may also be employed. Samples are then taken from the culture in order to identify and/or isolate the bacteria by conventionally known morphological tests and techniques.

The culture medium utilized with applicant's invention may be enriched media such as Todd-Hewitt Broth (Difco Laboratories, Detroit, Mich.), or universal media such as Triptic Soy Broth (Difco Laboratories, Detroit, Mich.) may be utilized. However, other well known culture media may also be employed in connection with the practice of the present invention.

Moreover, where the specimen to be tested contains a known bacterial inhibitor, i.e., the specimen came from an organism known to have been previously treated with a prescribed antibiotic, antibodies specific to the known antibiotic, including but not limited to monoclonal antibodies for said antibiotic, are utilized in applicant's invention at various dilutions. However, where a specimen contains an unknown number of unidentified bacterial inhibitors, various combinations of antibodies, including antibodies specific to certain antibiotics are utilized in the invention.

The antibody utilized within the present invention may be commercially obtained or prepared by conventionally known techniques. More particularly, ascites fluid containing monoclonal anti-penicillin G antibody 34-S1.1 and monoclonal anti-gentamycin antibody B26.16 may be obtained from Miles Laboratories, Elkhart, Indiana. Similarly, antibody against penicillin G and gentamycin may be prepared by standard methods demonstrated by Kohler and Milstein (Nature, 256, 496, 1975).

The following specific examples further illustrates the practice of the present invention.

EXAMPLE 1

A specimen was prepared by aseptically inoculating approximately 10 colony forming units (CFU) of Group A Streptococcus bacteria into a culture tube containing 0.7 ml. of culture medium (Todd-Hewitt broth, Difco Laboratories, Detroit, Mich.). Penicillin G (Sigma Chemical Co., St. Louis, Mo.) was added according the protocol in Table 1. Ascites fluid containing monoclonal anti-penicillin G antibody 34-S1.1 was obtained from Miles Laboratories, Elkhart, Ind. Control ascites fluid was obtained by standard methods from mice that had been injected with hybridoma cells producing an irrelevant antibody. Either the anti-penicillin G antibody or the control ascites fluid was added at a final concentration of 1:100 according to the protocol in Table 1. The volume of all cultures was adjusted to 1 ml. with culture media. The reaction mixture was incubated at 37° C. After 5 hours a sample from the reaction mixture was plated on Columbia agar with 5% sheep blood (Scott Laboratories, Fiskerville, Rhode Island) medium to determine the presence of the Group A Streptococcus bacteria. After 24 hours, the reaction mixture was observed for turbidity and the number of bacterial colonies growing on the blood agar plates was determined. The results were as follows:

TABLE 1

Detection of Group A Streptococcus Bacteria in Specimens Containing Penicillin G

| Bacteria | Penicillin G | Antibody (1:100) | CFU/ml 0 hr | CFU/ml 5 hr | Turbidity 24 hr |
|---|---|---|---|---|---|
| Streptococcus (Group A) | none | none | 70 | 3200 | + |
| Streptococcus (Group A) | 0.1 μg/ml | none | 70 | 0 | − |
| Streptococcus (Group A) | 0.1 μg/ml | control ascites | 120 | 10 | − |
| Streptococcus | 0.1 μg/ml | anti-penicillin G | 60 | 3600 | + |

As shown in Table 1, the addition of anti-penicillin G antibody to specimens containing 0.1 ug/ml of penicillin G allowed the Group A Streptococcus bacteria to grow to 3600 CFU after 5 hours, a result comparable to the growth of bacteria in the absence of penicillin G. The control cultures showed a decrease in the number of CFU present after 5 hours and the cultures did not develop turbidity indicative of bacteria growth.

EXAMPLE 2

An experiment similar to that performed in Example 1 was conducted. The results are shown in Table 2. In this example 2, the antibiotic was gentamycin sulfate (Sigma Chemical Co., St. Louis, Miss.) and the antibody was monoclonal anti-gentamycin antibody B26.16 which was obtained from Miles Laboratories, Elkhart, Ind. The results were as follows:

TABLE 2

Detection of Group A Streptococcus Bacteria in Specimens Containing Gentamycin

| Bacteria | Gentamycin | Antibody (1:10) | CFU/ml 0 hr | CFU/ml 5 hr | Turbidity 24 hr |
|---|---|---|---|---|---|
| Streptococcus (Group A) | none | None | 100 | 2,002 | + |
| Streptococcus (Group A) | 3 μg/ml | None | 160 | 20 | − |
| Streptococcus (Group A) | 3 μg/ml | control ascites | 50 | 220 | ± |
| Streptococcus (Group A) | 3 μg/ml | anti-gentamycin | 80 | 3360 | + |

As shown in Table 2, the addition of anti-gentamycin antibody to cultures containing the antibiotic allowed the bacteria to grow as well or better than bacteria cultured in the absence of gentamycin.

EXAMPLE 3

An experiment using the procedure shown in Example 1 was performed utilizing a combination of monoclonal anti-penicillin G antibody and monoclonal anti-gentamycin antibody. The results were as follows:

TABLE 3

Detection of Group A Streptococcus Bacteria in Specimens Containing both Penicillin G and Gentamycin

| Bacteria | Antibiotics* | Antibody (1:10) | CFU/ml 0 hr | CFU/ml 5 hr | Turbidity 24 hr |
|---|---|---|---|---|---|
| Streptococcus (Group A) | none | none | 100 | 7,200 | + |
| Streptococcus (Group A) | + | — | 90 | 0 | − |
| Streptococcus (Group A) | + | control ascites | 80 | 0 | − |
| Streptococcus | + | anti-penicillin | 70 | 6,800 | + |

TABLE 3-continued

Detection of Group A Streptococcus Bacteria in Specimens Containing both Penicillin G and Gentamycin

| Bacteria | Anti-biotics* | Antibody (1:10) | CFU/ml 0 hr | 5 hr | Turbidity 24 hr |
|---|---|---|---|---|---|
| (Group A) | | G + anti-gentamycin | | | |

*Gentamycin was added to a final concentration of 5 μg/ml and penicillin G was added at 1 μg/ml.

The results shown in Table 3 demonstrate that the combination of two monoclonal antibodies, each specific for a different antibiotic, allowed the bacteria to grow in the presence of those antibiotics. Specifically, the addition of anti-penicillin G and anti-gentamycin antibodies at a final dilution of 1:10 allowed the growth of Group A Streptococcus bacteria in the presence of both gentamycin (5 μg/ml) and penicillin G (1 μg/ml).

EXAMPLE 4

The test of Example 4 was conducted using the same procedure as described in Example 3, except that the body fluid specimen employed was human blood inoculated with approximately 900 CFU. The human blood was added to the culture tube to a final concentration of 10% by volume. The results were as follows:

TABLE 4

Detection of Group A Streptococcus Bacteria in Human Blood Inoculated With Group A Streptococcus Bacteria and Both Penicillin G and Gentamycin

| Bacteria | Human Blood | Anti-biotics* | Antibody (1:10) | CFU/ml 0 hr | 5 hr |
|---|---|---|---|---|---|
| Streptococcus (Group A) | 10% | none | none | 930 | 1,360 |
| Streptococcus (Group A) | 10% | + | none | 840 | 0 |
| Streptococcus (Group A) | 10% | + | control ascites | 790 | 0 |
| Streptococcus (Group A) | 10% | + | anti-penicillin G + anti-gentamycin | 920 | 28,000 |

*Penicillin G was added to a final concentration of 1 μg/ml and gentamycin was added at 5 μg/ml. The final volume of each tube was adjusted to 1 ml.

The results shown in Table 4 demonstrate that the specific monoclonal antibodies are able to neutralize gentamycin and penicillin even in the presence of 10% human blood. This example demonstrates that the process of neutralizing antibiotics with specific antibodies is applicable for testing human blood specimens for the presence of bacteria, even when the blood sample contains antibiotics.

EXAMPLE 5

The test of Example 5 was conducted using the same procedure as described in Example 4 except that the body fluid specimen employed was human urine (which had been filter-sterilized prior to use) and the culture medium employed was Tryptic Soy Broth (Difco Labs, Detroit, Mich.). The human urine was added to a final concentration of 10% and the cultures were seeded with approximately 30 CFU of bacteria.

TABLE 5

Detection of Group A Streptococcus Bacteria in Human Urine Specimens Containing Both Penicillin G and Gentamycin

| Bacteria | Anti-biotics* | Antibody (1:10) | CFU/ml 0 hr | 5 hr | Turbidity (24 hr) |
|---|---|---|---|---|---|
| Streptococcus (Group A) | None | None | 10 | 8,200 | + |
| | + | None | 40 | 0 | — |
| | + | Control Ascites | 70 | 0 | — |
| | + | Anti-pencillin G + Anti-gentamycin | 20 | 9,000 | + |

*Gentamycin was added to a final concentration of 5 μg/ml and penicillin G was added at 1 μg/ml. The final volume was adjusted to 1 ml with Tryptic Soy Broth.

The results shown in Table 5 demonstrate that the specific monoclonal antibodies are able to neutralize gentamycin and penicillin even in the presence of 10% human urine. Therefore, this example demonstrates that the process of neutralizing antibiotics with specific antibodies is applicable for testing human urine specimens for the presence of bacteria, even when the urine sample contains antibiotics.

While there have been described herein what are at present considered to be the preferred embodiments of this invention, it will be apparent to those skilled in the art that various changes and modifications may be made therein without departing from the invention, and it is, therefore, intended in the appended claims to cover all such changes and modifications as fall within the true spirit and scope of the invention.

What is claimed is:

1. A method for determining the presence of bacteria in a body fluid specimen containing bacterial inhibitors, which method comprises:
   a. providing a body fluid specimen containing bacterial inhibitors;
   b. adding growth media for said bacteria to the body fluid specimen;
   c. adding antibodies specific to the bacterial inhibitors to the body fluid specimen to neutralize the effectiveness of the bacterial inhibitors; and
   d. incubating said reaction mixture and thereafter determining the presence of bacteria in the body fluid specimen.

2. The method of claim 1 wherein the presence of bacteria in the body fluid specimen is determined by the turbidity of the reaction mixture.

3. The method of claim 1 wherein the presence of bacteria in the body fluid specimen is determined by plating a sample of the reaction mixture on growth media for said bacteria, and after an incubation period, ascertaining the bacteria colonies formed.

4. The method of claim 1 wherein said bacteria inhibitors are antibiotics.

5. The method of claim 4 wherein said antibiotic is penicillin G.

6. The method of claim 4 wherein said antibiotic is gentamycin.

7. The method of claim 1 wherein said antibodies are specific monoclonal antibodies to the bacterial inhibitors.

8. The method of claim 7 wherein said monoclonal antibodies are monoclonal anti-penicillin G antibodies.

9. The method of claim 7 wherein said monoclonal antibodies are monoclonal anti-gentamycin antibodies.

10. The method of claim 1 wherein said body fluid specimen is blood.

11. The method of claim 1 wherein said body fluid specimen is urine.

12. The method of claim 1 wherein said bacteria is Streptococcus (Group A) bacteria.

13. The method of claim 1 wherein said growth media is Todd-Hewitt Broth.

14. The method of claim 1 where said growth media is Triptic Soy Broth.

* * * * *